(12) United States Patent
Bittner et al.

(10) Patent No.: US 12,405,201 B2
(45) Date of Patent: Sep. 2, 2025

(54) METHOD FOR DETECTING AEROSOL PARTICLES IN AMBIENT AIR, INVOLVES IRRADIATING ANALYSIS VOLUME WITH RADIATION MODULATED WITH MODULATION FREQUENCY TO GENERATE SOUND PRESSURE WAVES

(71) Applicant: Hahn-Schickard-Gesellschaft für angewandte Forschung e. V., Villingen-Schwenningen (DE)

(72) Inventors: Achim Bittner, Heilbronn (DE); Alfons Dehé, Reutlingen (DE); Rebecca Wienbruch, Aach (DE)

(73) Assignee: Hahn-Schickard-Gesellschaft für Angewandte Forschung e. V., Villingen-Schwenningen (DE)

( * ) Notice: Subject to any disclaimer, the term of this patent is extended or adjusted under 35 U.S.C. 154(b) by 331 days.

(21) Appl. No.: 18/007,004

(22) PCT Filed: Jul. 21, 2021

(86) PCT No.: PCT/EP2021/070394
§ 371 (c)(1),
(2) Date: Jan. 26, 2023

(87) PCT Pub. No.: WO2022/023141
PCT Pub. Date: Feb. 3, 2022

(65) Prior Publication Data
US 2023/0266222 A1    Aug. 24, 2023

(30) Foreign Application Priority Data

Jul. 29, 2020    (EP) .................................... 20188316

(51) Int. Cl.
*G01N 15/06*    (2024.01)
*G01N 15/075*    (2024.01)
(Continued)

(52) U.S. Cl.
CPC ......... *G01N 15/06* (2013.01); *G01N 33/0027* (2013.01); *G01N 15/075* (2024.01)

(58) Field of Classification Search
CPC ................. G01N 15/01; G01N 33/483; G01N 21/6458; G01N 21/253; G01N 27/628;
(Continued)

(56) References Cited

U.S. PATENT DOCUMENTS 9,964,470 B2 *  5/2018  Sharp .................. G01N 1/2273
2003/0159498 A1  8/2003  Small
(Continued)

FOREIGN PATENT DOCUMENTS

DE          4130639 A1    3/1993
WO      WO 93/06457 A1    4/1993
WO    WO 2015/020611 A1    2/2015

OTHER PUBLICATIONS

International Search Report in PCT/EP2021/070394 issued Sep. 24, 2021.

*Primary Examiner* — Brandi N Hopkins
(74) *Attorney, Agent, or Firm* — Knobbe, Martens, Olson & Bear, LLP

(57) ABSTRACT

A method for detecting aerosol particles in ambient air with a photoacoustic gas sensor, wherein an analysis volume is present in the beam path of a modulable emitter such that the emitter can use modulable radiation to excite aerosol particles in the analysis volume to form sound pressure waves which are detectable by means of the sensor. Using the modulable emitter, the analysis volume is irradiated with the modulated radiation to generate sound pressure waves. The generated sound pressure waves are measured by the sensor, whereby the presence and/or concentration of the aerosol particles in the ambient air is determined on the basis of the measurement results. In some embodiments, the aerosol
(Continued)

particles are bioaerosols, such as pollen, spores, bacteria and viruses.

11 Claims, 2 Drawing Sheets

(51) Int. Cl.
  *G01N 21/17* (2006.01)
  *G01N 33/00* (2006.01)
(58) Field of Classification Search
  CPC ........ G01N 33/497; G01N 1/10; G01N 21/76; G01N 30/72; G01N 15/0656; G01N 15/10; G01N 21/65; G01N 15/075; G01N 15/0205; G01N 15/143; G01N 15/06; G01N 33/0027; Y02A 50/30
  USPC ........................................................ 73/24.02
  See application file for complete search history.

(56) References Cited

U.S. PATENT DOCUMENTS

| | | | |
|---|---|---|---|
| 2011/0108023 A1* | 5/2011 | McKinney | A61M 16/026 128/200.14 |
| 2014/0053629 A1* | 2/2014 | Cahill | G01N 33/0063 73/28.01 |

\* cited by examiner

Fig. 1

Fig. 2

| Size | Viren | Pollen | Bacteria | Soot particles |
|---|---|---|---|---|
|  | 22 – 330 nm | 10 – 100 µm | 0,1 – 700 µm | 10 - 300 nm |

# METHOD FOR DETECTING AEROSOL PARTICLES IN AMBIENT AIR, INVOLVES IRRADIATING ANALYSIS VOLUME WITH RADIATION MODULATED WITH MODULATION FREQUENCY TO GENERATE SOUND PRESSURE WAVES

In a first aspect, the invention relates to a method for detecting aerosol particles in ambient air by means of a photoacoustic gas sensor, wherein an analysis volume is present in the beam path of a modulable emitter such that the emitter can use modulable radiation to excite aerosol particles in the analysis volume to form sound pressure waves which are detectable by the sensor. Using the modulable emitter, the analysis volume is irradiated with the modulated radiation to generate sound pressure waves. The generated sound pressure waves are measured by the sensor, whereby the presence and/or concentration of the aerosol particles in the ambient air is determined on the basis of the measurement results. Particularly preferably, the aerosol particles are bioaerosols, preferably pollen, spores, bacteria or viruses. In a further aspect, the invention relates to a photoacoustic gas sensor suitable for carrying out the method.

BACKGROUND AND PRIOR ART

The invention relates to the field of detection of aerosol particles in ambient air, in particular biological aerosols such as bacteria, spores or viruses.

Infectious diseases are one of the most common causes of death worldwide. Pneumonia, diarrheal diseases, AIDS, tuberculosis and malaria account for most of the deaths.

The treatment of infectious diseases is becoming increasingly difficult due to the rise in pathogens that are resistant to drugs (antibiotics, antivirals). The main causes of the increasing development of resistance are the improper use of antibiotics and the inconsistent application of necessary hygiene measures to prevent infections.

In addition, the outbreak of the Covid 19 pandemic in 2020 strikingly demonstrates that emerging infectious diseases for which neither therapies nor vaccine protection are available can threaten the very foundations of human societies.

Aerogenic infectious diseases pose a particular risk among infectious diseases. Aerogenic infectious diseases are infectious diseases that are transmitted via the airway (aerogenic) by inhalation of suspended particles containing pathogens. Aerogenic infectious diseases include, for example, tuberculosis, pollen, measles, chickenpox, influenza or Covid 19.

Globally, over 10 million people contract tuberculosis each year alone, of which an average of 1.5 million die (Word Health Organization WHO, *Global tuberculosis report* 2019). Covid 19 has been shown to have infected over 15 million people worldwide in the months from March to July 2020 alone, with over 600,000 deaths recorded (Source: WHO).

The difficulty of controlling aerogenic infectious diseases and their high degree of infectivity is closely related to their spread. Transmission of aerogenic infectious diseases does not require direct contact between people, but can occur indirectly via aerosols spreading in the ambient air.

Airborne particles can remain airborne for some time after initial aerosolization and therefore potentially expose a much higher number of susceptible individuals to a risk of infection.

Depending on environmental factors (e.g., outdoor meteorological conditions, indoor pressure differences, etc.), airborne particles can easily be transported over many meters and can also remain indoors for several hours (Fernstrom A. et al 2013).

Direct determination of the pathogen load in the ambient air can therefore represent an important pillar in the prevention or containment of aerogenic infectious diseases. Based on a measurement of the pathogen load, for example, early warning systems can be established within private or public buildings and effectively prevent infection chains.

Known techniques for the detection of bacteria or virus particles in air are often time-consuming or require complex instrumentation or sample manipulations (antibody binding, electrochemical reactions).

Traditional approaches use collection devices for ambient air. In these, the viruses or bacteria are immobilized using suitable substrates. Molecular biological identification of the pathogens can be carried out, for example, by means of a polymerase chain reaction (see, among others, Schafer et al 1999 for the detection of airborne tubercle bacilli.)

Tobias et al 2005 propose the use of mass spectroscopy for the detection of aerogenic tuberculosis bacteria. Senguptaa, A 2007 use a surface-enhanced Raman spectroscopy for the detection of bioaerosols. For this purpose, instrumentation was developed to detect and characterize airborne pollen and bacteria by injecting a bioaerosol into a nanocolloidal suspension of silver particles using a micropump. The biological particles are mixed with the silver colloid to deposit the metallic particles on the surface of the bioanalyte and then their spectra are measured. From Kyu-Tae Park et al 2015, an approach for detection is known, which is based on electro-aerodynamic deposition and a field-effect transistor.

In addition, there are also a number of fluorescence-based approaches for the detection of biological particles in aerosols. Here, monochromatic light (continuous or pulsed) is typically used to study the fluorescence properties of individual particles passing through the instrument in the air. For the detection of biological molecules, it is possible to exploit the fact that the autofluorescence, i.e., intrinsic fluorescence, of some biomolecules can indicate the presence of biological material, while the intensity of most non-biological aerosols is low. However, similarities in the spectral emission of different biological particles result in reduced specificity (Huffmann et al. 2020).

In light of known techniques, there is thus a need for improvement, which in particular reduces the complexity of instrumentation or sample manipulations and yet reliably allows detection in particular of viruses or bacteria in ambient air.

Photoacoustic spectroscopy (PAS) is an established technique for the detection of very fine concentrations of gases and has a variety of applications. One example is the detection of $CO_2$, which plays a role in research and climate control technology. The concentration of exhaust gases in the air, for example, can also be measured in this way. Military applications are also relevant, where the smallest concentrations of toxic gas can be detected.

Photoacoustic spectroscopy uses intensity-modulated infrared radiation with frequencies in the absorption spectrum of a molecule to be detected in a gas. If this molecule is present in the beam path, modulated absorption takes place, leading to heating and cooling processes whose time scales reflect the modulation frequency of the radiation. The heating and cooling processes lead to expansions and contractions of the gas, causing sound waves at the modulation frequency. These can then be measured by sound detectors, such as microphones, or flow sensors.

The use of PAS for specific detection of viruses or bacteria within aerosols is largely unresearched.

U.S. Pat. No. 7,710,566 B2 PAS proposes to use PAS for the detection of dust particles. Detection of viruses or bacteria is not described. Also, the equipment complexity is high.

Lack et al. 2007 is a research article on photoacoustic spectroscopy of aerosols. The aim is to use photoacoustic spectroscopy to investigate the absorption properties of aerosols with respect to global warming. Detection of viruses or bacteria using PAS is not disclosed.

WO 2015/020611 A1 proposes an apparatus and a method for the detection of aerosol particles. A fluid enters a measurement chamber via an inlet, and the chamber is irradiated by a radiation source. The device comprises a MEMS resonator, which aims to detect the aerosol particles based on their absorption characteristics via preferably two modes, a photoacoustic mode and a bulk acoustic wave (BAW) mode. In the photoacoustic mode, the photoacoustic effect or the thermoacoustic effect is used to detect aerosol particles. The MEMS resonator detects a sound pressure wave caused by the light absorption of the aerosol particles. The aerosols are dust or soot particles. The use of photoacoustic spectroscopy to detect bioaerosols, such as viruses, bacteria or pollen is not disclosed.

DE 41 30 639 A1 concerns a device for the photoacoustic detection of graphite and soot particles. Via a gas pump, the aerosols enter a resonant photoacoustic cell which is irradiated with a modulable semiconductor diode laser. Preferably, not the first resonant mode but the resonant frequencies of the next higher mode are used for modulation in order to avoid low-frequency interference. DE 41 30 639 A1 aims to provide a compact and mobile soot detection system with a high detection limit. The detection of bioaerosols, in particular pollen, spores, bacteria or viruses, is also not disclosed in DE 41 30 639 A1. U.S. Pat. No. 9,964,470 B2 discloses a method and a system to control the air quality of a room. The method uses air containment sensors, which are part of a multipoint air monitoring system. By means of an improved approximation of a true indoor air containment level, a more precise adjustment of the necessary ventilation and air supply shall be made possible. The air containment sensors are not described in detail.

U.S. Pat. No. 9,964,470 B2 lists a variety of measurement methods, mentioning a photoacoustic measurement principle along with a number of other measurement methods (electrochemical, optical, etc.). The air containments to be monitored are said to include various particles, with bioaerosols such as viruses, bacteria, etc. also mentioned. U.S. Pat. No. 9,964,470 B2 does not comprise any direct teaching on the use of a photoacoustic measurement principle for the detection of bioaerosols, such as fungi, viruses or bacteria. Rather, with regard to the prior art, a person skilled in the art would assume that electrochemical methods, for example, are used for the detection of fungi, viruses or bacteria, which are also mentioned in the listing of possible measurement methods. A person skilled in the art will not find any indication that a photoacoustic measurement principle can be used for the detection of bioaerosols in U.S. Pat. No. 9,964,470 B2.

Thus, in light of the prior art, there is a need for improved or alternative methods or devices for detecting aerosol particles in ambient air.

Objective of the Invention

The objective of the invention is to provide a method as well as a suitable apparatus for the detection of aerosol particles in ambient air without the disadvantages of the prior art. In particular, one objective of the invention was to provide an improved method which can measure aerosol particles, in particular bioaerosols, reliably, quickly, inexpensively and without complex sample manipulation or instrumentation.

SUMMARY OF THE INVENTION

The objective is solved by the features of the independent claims. Advantageous embodiments of the invention are described in the dependent claims.

In one aspect, the invention relates to a method for detecting aerosol particles in ambient air, comprising the following steps
  a. Providing a photoacoustic gas sensor comprising
     a modulable emitter, in particular a MEMS emitter
     an analysis volume which is in fluid communication with the ambient air
     a sensor for the detection of sound pressure waves, in particular a MEMS sensor
     wherein the analysis volume is present in the beam path of the emitter so that the emitter can use modulable radiation to excite aerosol particles in the analysis volume to form sound pressure waves which are detectable by the sensor,
  b. Irradiating the analysis volume with radiation modulated with a modulation frequency to generate sound pressure waves
  c. Measuring the generated sound pressure waves by means of the sensor
  d. Determining the presence and/or concentration of aerosol particles in the ambient air based on the results of the measurement
  where the aerosol particles are preferably bioaerosols.

The method according to the invention is characterized by the fact that the presence and/or concentration of aerosol particles can be reliably detected by means of an extremely compact and robust photoacoustic gas sensor, preferably based on MEMS technology. In contrast to many approaches in the prior art, it is advantageous that no complex sample manipulation is required for this purpose. Instead, by tuning the wavelength of the emitted radiation to the absorption behavior of the aerosol particles, the presence and/or concentration of the aerosol particles can be reliably detected, especially with regard to biological structures such as viruses or bacteria.

The method is thus characterized by a simple and fast detection of aerosol particles in the air by a photoacoustic effect. The low-cost implementation using a compact MEMS-based sensor results in an extremely wide range of possible applications.

The method can be used, for example, in public spaces, public transport, but also in private environments or ventilation systems to reliably monitor the ambient air with regard to the presence and/or concentration of aerosol particles, in particular viruses or bacteria. In the event that previously defined thresholds are exceeded, a warning can be issued and/or measures can be taken to prevent the spread of potentially hazardous aerosol particles.

The method is of particular importance for the medical sector, for example as an early warning system in medical waiting rooms or in various areas of a hospital. The simplicity of the method and the possibility of a low-cost implementation thus allow in particular a broad coverage for monitoring the ambient air with regard to the spread of pathogenic particles.

In particularly preferred embodiments of the method, the aerosol particles are bioaerosols, preferably pollen, spores, bacteria and viruses. The method can also be used to detect soot particles or dust particles. However, the method gains particular importance through the possibility, recognized by the inventors, that a PAS can also be used for the specific detection of complex biological structures such as bacteria, viruses, pollen or even spores.

The basic features and essential components of a photoacoustic spectrometer for the analysis of gas are known to the person skilled in the art. A modulable emitter generates electromagnetic radiation, in particular in the infrared wavelength range, and is preferably arranged and configured in such a way that the radiation emitted by the emitter is substantially or at least partially incident on the gas to be analyzed in the measuring cell.

If the modulated irradiation takes place with an infrared wavelength corresponding to the absorption spectrum of a molecule of a gas component present in the gas mixture, modulated absorption takes place, which leads to heating and cooling processes whose time scales reflect the modulation frequency of the radiation. According to the photoacoustic effect, the heating and cooling processes lead to expansions and contractions of the gas component whereby the gas component can be excited to form sound pressure waves with substantially the modulation frequency. These can be measured by the sound detector. The power of the sound waves is preferably directly proportional to the concentration of the absorbing gas component.

Surprisingly, it was found that the photoacoustic effect can be similarly extended to complex and, compared to gas components, macroscopic biological structures and is thus suitable for the detection of bioaerosols.

In a preferred embodiment, selective excitation and detection of aerosol particles is accomplished by tuning one or more wavelengths of emitted radiation to the absorption behavior of aerosol particles, particularly preferably bioaerosols such as pollen, spores, bacteria, or viruses.

For this purpose, it may be preferred that reference data on the wavelength-dependent photoacoustic absorption behavior of the aerosol particles be recorded to optimize the wavelength-dependent excitation.

Advantageously, bioaerosols such as pollen, spores, bacteria and viruses exhibit a characteristic photoacoustic fingerprint for this purpose. Thus, wavelength-dependent distinct photoacoustic resonances occur for the investigated biological structures.

This shows that often for wavelengths in the near-infrared range for bioaerosols, such as bacteria, viruses or pollen, a characteristic photoacoustic signal can be recorded at one or more wavelengths.

However, certain components of the biological structures can also be selectively excited in the UV range. Carotenoids in the pollen coat absorb in the blue range (wavelengths above 500 nm) of visible light. Proteins, biomacromolecules, and nucleic acids have chromophores that generally absorb at wavelengths below 300 nm (UV range). Proteins in the viral envelope thus absorb in the UV range. Water and organic structures also absorb the low-energy infrared light particularly well.

However, test series show that wavelengths above 170 nm are preferred for the investigation of aerosols, especially bioaerosols, due to the high water content.

In a particularly preferred embodiment of the method, the aerosol particles are bioaerosols, preferably pollen, spores, bacteria or viruses, and the one or more wavelengths of the emitter are preferably selected for selective excitation from a range between 170 nm and 10 μm, preferably between 200 nm and 1000 nm.

Preferred exciting wavelengths are in the aforementioned range, although intermediate ranges may also be preferred, such as 200 nm to 300 nm, 300 nm to 400 nm, 400 nm to 500 nm, 600 nm to 700 nm, 700 nm to 800 nm, 800 nm to 900 nm, 900 nm to 1000 nm, 1000 nm to 1500 nm, 1500 nm to 2000 nm, 2500 nm to 3000 nm, 3000 nm to 4000 nm, 4000 nm to 5000 nm, or even 5000 nm to 10 000 nm. A person skilled in the art will recognize that the aforementioned parameter ranges can also be combined to obtain other preferred ranges, such as 200 nm to 1500 nm, 500 nm to 900 nm, or 300 nm to 2000 nm.

The selection of the one or more wavelengths for a specific bioparticle, for example a virus, pollen and/or bacterium can preferably be determined by means of test series as described above.

Particularly good results can be obtained with excitation with two, three, four, five or more different wavelengths, in particular from the range between 170 nm and 10 μm, preferably 200 nm and 1000 nm. Here, it may be preferred that the selective excitation with the two, three, four, five or more different wavelengths takes place at two, three, four, five or more different times and the presence and/or concentration of the aerosol particles in the ambient air is determined on the basis of the measured sound pressure waves at the two, three, four, five or more different wavelengths.

According to the invention, it was found that due to the complex composition of biological structures, for example with regard to their protein composition, different biological structures can be assigned highly detailed photoacoustic fingerprints.

Although biological aerosol particles, such as viruses, bacteria or pollen, may in principle comprise similar proteins, such that photoacoustic absorptions occur in similar wavelength ranges, the differing proportions of proteins leads to particularly distinct PAS signals at the different wavelengths. Information about the wavelength-dependent position of the PAS signals as well as their respective amplitude thus allows a particularly precise determination of the presence or concentration of specific aerosol particles, analogous to a spectral fingerprint.

The term PAS signal or photoacoustic signal preferably means the measurement results of the sensor via the sound pressure waves generated in the analysis volume, in particular sound pressure waves with a frequency which substantially corresponds to the modulation frequency of the exciting emitter.

In preferred embodiments, the reference data are obtained using calibration measurements in which the concentration of the aerosol particles to be detected in the ambient air is known and controlled. For this purpose, the photoacoustic gas sensor can, for example, be placed in a calibration chamber in which a defined concentration of aerosol particles is present under laboratory conditions.

To obtain the reference data, a wavelength-dependent detection of the photoacoustic signals is preferably carried out over a defined wavelength range, for example from 170 nm to 10 μm, preferably 170 nm to 1000 nm. Based on the detected peaks of the photoacoustic signals, one or more wavelengths are defined for selective excitations as well as thresholds for the corresponding photoacoustic signals, which indicate an increased concentration of the aerosol particles in the ambient air.

Advantageously, the proposed method can detect a plurality of even complex aerosol particles in the ambient air.

For the purposes of the invention, the term aerosol generally refers to a collection of liquid or solid particles (or particulates) that are suspended in a gaseous medium long enough to be observed and measured. The particles are also referred to as aerosol particles or suspended particles. Aerosol particles typically range in size from about 0.001 µm to about 100 µm (see Kulkarni et al., Aerosol Measurement, 3rd ed., John Wiley & Sons, Inc., 2011).

The term ambient air generally refers to a gas (or gaseous fluid, or gas phase fluid). The gas may or may not contain liquid droplets or vapor, and may or may not contain aerosol particles. An aerosol can therefore also be considered to contain particles and a gas that entrains or carries the particles.

As used herein, the term bioaerosol generally refers to an aerosol in which one or more bioparticles are suspended or carried. The term bioparticle generally refers to a biological material or the combination of a biological material and a non-biological particle on which the biological material is carried. That is, a biological material may itself be a particle freely suspended in an aerosol, or it may be carried on a non-biological particle such that the biological material and the non-biological particle are suspended together in the aerosol.

The biological material may be carried on the non-biological particle by any mechanism, such as entrapment, embedding, adhesion, adsorption, attraction, affinity, etc. Examples of biological material include, but are not limited to, spores (e.g., fungal spores, bacterial spores, etc.), fungi, molds, bacteria, viruses, biological cells or intracellular components, biologically derived particles (e.g., skin cells, detritus, etc.), etc.

Bioaerosols may include pathogenic or non-pathogenic, live or dead bacteria and fungi, viruses, high molecular weight allergens, bacterial endotoxins, mycotoxins, peptide glycans, beta(1-3) glucans, pollen, plant fibers, etc. Exposure to bioaerosols is associated with a number of diseases such as infectious diseases and respiratory diseases. Other diseases and conditions have been associated with exposure to bioaerosols, such as cancer, (Bioaerosol Health Effects and Exposure Assessment: Progress and Prospects, J. Douwes, P. Thorne, N. Pearce, and D. Heederik, Institute for Risk Assessment Sciences, Division of Environmental and Occupational Health, Utrecht University, The Netherlands; Centre for Public Health Research, Massey University Wellington Campus, Wellington, New Zealand; University of Iowa College of Public Health, Department of Occupational and Environmental Health, IA, USA).

The biological microorganisms or particles can reach the ambient air in different ways: For example, as isolated particles without a significant amount of accompanying substances; adhering to solid particles, e.g., skin flakes, plant parts, soil particles, or even in droplets.

Droplet transmission in particular represents a significant infection route for the transmission of aerogenic infectious diseases. During exhalation, speech, vomiting, sneezing and coughing, saliva and other liquid secretions of the respiratory tract, such as nasal secretions and sputum, are released into the environment as droplets by nebulization.

The term bioaerosol is intended to cover all the above-mentioned floating mechanisms. I.e. the term bioaerosol is to be understood in particular as individual bioparticles, such as freely floating fungal spores, bacteria and yeasts which adhere to other particles and float with them (skin flakes, dust, parts of plants, hair, feathers, fibers of clothing) or droplets in which bacteria or viruses are present.

In a preferred embodiment of the invention, the aerosol particles to be detected are viruses.

The term "virus" as used herein preferably refers to a small infectious agent that can only replicate in the living cells of organisms and may include virions as well as virus particles. Preferably, viruses may have a diameter of 20-330 nm.

Non-limiting examples of virus families are Adenoviridae, Arenaviridae, Bunyaviridae, caliciviridae, circoviridae, coronaviridae, deltavirus, Siphoviridae, filoviridae, flaviviridae, hepadnaviridae, hepeviridae, herpesviridae, orthomyxoviridae, paramyxoviridae, picomaviridae, poxyviridae (poxviruses), reoviridae, retroviridae, and rhabdoviridae.

Particularly preferred are viruses that are transmitted by air and are responsible for various diseases in humans, animals and plants, such as chickenpox (by the varicella-zoster virus, VZV), common cold (by the coronavirus), pulmonary diseases, especially COVID 19 caused by the SARS-CoV-2 virus, influenza in humans and animals (influenza viruses), measles (measles viruses), rubella rinderpest (caused by the morbillivirus) or respiratory diseases in cattle (caused by the bovine respiratory syncytial virus, BRSV), or even plant viruses that are aerosolized from the soil.

In a preferred embodiment of the invention, the aerosol particles to be detected are bacteria. The size, shape or type of bacteria that can be detected by the proposed method varies widely. For example, the bacteria may have a diameter between about 0.1 and 700 µm, preferably between about 0.6 and 1.0 µm.

Bacteria occur in various external forms: spherical, called cocci (*Micrococcus*), cylindrical, called rods (*Bacillus, Escherichia*) with more or less rounded ends, helical (*Spirillae, Spirochaetes*), with stalks (*Caulobacter*), with appendages (*Hyphomicrobium*), forming multicellular trichomes (*Caryophanon, Oscillatoria*), forming long, branched filaments called hyphae, which branch and form a filamentous mass called mycelium (*Streptomycetes*), and structures with several irregularly arranged cells (*Pleurocapsa*). Bacteria can also occur in aggregates: chains of spheres (*Streptococcus*), planar arrangement of spherical cells (*Merismopedia*), regular three-dimensional arrangement of spheres (*Sarcina*), rod chains (*Streptobacillus*), rod chains enclosed in tubes (*Leptothrix*).

Particularly preferred are bacteria, which are transmitted via the airway and are responsible for various diseases in humans, animals and plants, such as tuberculosis (by *Mycobacterium tuberculosis*), diphtheria (*Corynebacterium diphtheriae*), scarlet fever, meningitis (by *streptococci*) or pneumonia (by *pneumococci*, a subspecies of *streptococci*).

In a preferred embodiment of the invention, the aerosol particles to be detected are fungi or fungal spores. Infectious diseases which are triggered by fungi are also called mycoses or fungal diseases. These include both superficial mycoses, for example mycoses of the skin or mucous membranes, and systemic mycoses, in which the fungal pathogens usually enter the bloodstream via the lungs.

By means of the proposed method, it is advantageously possible to detect fungi or fungal spores that are transmitted via the ambient air, such as mold spores. In particular, fungal infections pose a high risk for persons with a weakened immune system due to a pre-existing disease (including HIV, diabetes) or due to the use of immunosuppressive drugs (in the case of autoimmune diseases). Continuous monitoring of the presence or concentration of fungi or fungal spores can therefore be used in the medical field, for example in hospitals, to prevent secondary diseases.

In a preferred embodiment of the invention, the aerosol particles to be detected are pollen. Pollen is mostly a flour-like mass formed in the stamens of seed plants and consists of pollen grains. Pollen grains are very diverse in size, shape, and surface structure, and in many cases can be assigned to species or at least genera based on these characteristics. Most pollen grains are between 10 and 100 micrometers in size.

Pollen often contains allergenic proteins, which is the main cause of allergic diseases such as hay fever or asthma in temperate climates (Marsh, 1975). As aerogenic particles, pollen can disperse in the air for hours or days over many kilometers. Routine monitoring of the concentration of pollen in the ambient air by means of the proposed method thus allows the establishment of an early warning system, which can protect potentially endangered persons from allergic overreaction.

The inventors have recognized that bioaerosols (including bacteria, viruses, spores, or pollen) can be reliably detected with a photoacoustic gas sensor comprising a modulable emitter and a sound pressure detector.

A modulable emitter preferably refers to an apparatus that emits electromagnetic radiation.

This radiation preferably has a wavelength range in the infrared (IR) range, in particular between about 700 nanometers (nm) and 10 µm, in the ultraviolet range, in particular between 170 nm and 380 nm, or also in the visible range (VIS), in particular between 380 nm and 700 nm.

In particular, the spectrum is chosen to correspond to the preferred field of application of the photoacoustic spectroscopy.

In particular, it is preferred that the oscillations of the excitation of the aerosol particles to be spectroscoped and/or detected correspond to a preferred spectral range, which is dependent on the constituents of the aerosols, especially in the case of bioaerosols.

Carotenoids in the pollen coat primarily absorb in the visible blue range (wavelengths above 500 nm). Proteins, biomacromolecules and nucleic acids often have chromophores that absorb only at wavelengths below 300 nm (UV range). Proteins in the viral envelope often absorb in the UV range as well. Organic molecules, which occur in bacteria and viruses, also absorb low-energy infrared light (especially near-infrared light) particularly well.

In a preferred embodiment, the emitter is an infrared emitter. Particularly preferred wavelength ranges of the infrared radiation are 700 nm to 10 µm, preferably 700 nm to 3 µm or also 700 nm to 1 µm.

For generating the infrared radiation, it is preferred that thermal energy is provided in the form of a heating element. A (micro) heating element is particularly preferred. A microheating element is preferably understood to mean a heating element with dimensions of the order of micrometers (µm). Here, the heating element comprises a heatable layer of a conductive material which produces joule heat when an electric current flows through it. The heat produced is preferably dependent on the ohmic resistance of the element and the square of the current or the square of the applied voltage and the inverse ohmic resistance, depending on whether a current or voltage source is used. A thermal source of infrared radiation has advantageous properties for PAS, such as broadband emission, through which a wide variety of gas atoms or molecules can be excited with only one light source. At the same time, a thermal IR emitter is particularly inexpensive, easy to manufacture and durable.

In a state of equilibrium, the heat produced is equal to the heat losses due to thermal conduction, convection and thermal radiation (synonym: thermal radiation, infrared radiation), which is emitted at the outer boundary surfaces of the heatable layer through which the current flows. As is known to the person skilled in the art, the heat produced causes, among other things, thermal radiation, in particular by thermal movement of particles, which results, for example, in acceleration of charge carriers and/or oscillating dipole moments. Thus, infrared radiation can be specifically generated by a current-carrying heatable layer. The heatable layer is preferably made of metal, for example tungsten or platinum. By applying a suitable voltage and the resulting current flow, Joule heat and thus ultimately infrared radiation is generated.

The radiation spectrum of a heated body can preferably be described approximately by Planck's radiation law, whereby the differences of a real heatable layer to a black body are known to the person skilled in the art, for example the emissivity or the real deviation from a thermal equilibrium of the body. Despite these deviations, the generated spectrum and its intensity are substantially delineated by the temperature and the radiating area according to Planck's radiation law.

Terms such as substantially, approximately, about, etc. preferably describe a tolerance range of less than ±20%, preferably less than ±10%, even more preferably less than ±5% and in particular less than ±1%. Indications of substantially, approximately, about, etc. always also disclose and include the exact value mentioned.

Thus, a person skilled in the art can achieve a preferred spectrum with a preferred intensity distribution by precisely designing a (micro) heating element. For this purpose, in addition to the material and the geometric design of the heating element, the electrical energy made available, as well as the magnitude of the heat losses from the heating element in addition to the thermal radiation are preferably decisive. The magnitude of these heat losses is determined, for example, by the thermal conductivity between the heating element and the adjacent materials and/or fluids as well as their heating capacity and the size of the boundary surface(s).

An IR emitter in the form of a heating element is particularly cost-effective and robust, while at the same time the spectral width of the emission allows a large number of aerosol particles to be detected in a PSA. By means of a preferably tunable bandpass filter, narrower spectra can be selected from the broad emission spectrum if required.

The infrared radiation of an infrared emitter can preferably also be generated by a light-emitting diode (LED) emitting in the desired infrared spectral range and/or a laser.

In a preferred embodiment, the emitter is a VIS and/or UV emitter. Particularly preferred wavelength range of UV radiation is 170 nm to 380 nm, while a preferred wavelength range between 380 nm and 700 nm can be covered by the VIS emitter (visible emitter in the visible range).

Particularly preferably, an emitting light-emitting diode (LED) and/or a laser can be used for a VIS or UV emitter.

LEDs are nowadays available for a wide range of wavelengths at low cost in a compact design. Lasers preferably have a narrow emission spectrum, such that preferably only absorption lines of the aerosol particles, preferably of the bioaerosols, that exactly match this spectrum can be excited and thus detected.

The emission of the emitter is preferably in the form of a beam, which is oriented in a preferred direction in the form of a straight line. The term beam preferably refers to the focused portion of the radiation along the preferred beam direction of the emitter, whereby in particular the areas of greatest intensity along this direction define the beam. Intensity is preferably defined as area power density and preferably has the unit of watts per square meter or abbreviated $W/m^2$.

Additional components, such as lenses, may be integrated into the emitter or attached externally to provide for beam focusing or collimation. A person skilled in the art knows how to shape the emission profile of the radiation source by designing the emitter as well as by using additional components in such a way that a desired beam profile as well as a desired beam direction result.

Preferably, the modulable emitter can function without additional lenses, or can be a system comprising a radiation source and at least one lens for collimating the beam.

The emitter is modulable, which means that the intensity of the emitted radiation, preferably the intensity of the beam can be changed in a controllable manner over time. The modulation shall preferably cause a temporal change of the intensity as a measurable variable. This means, for example, that there is a difference in intensity over time between the weakest intensity measured within the measurement period and the strongest intensity measured within the same period that is greater than the sensitivity of an instrument typically used for measuring or determining intensity in the radiation spectrum. Preferably, the difference is significantly greater than a factor of 2, more preferably 4, 6 or 8 between the strongest and weakest adjustable intensity.

Particularly preferably, the intensity of the modulated beam is modulated for one or more predetermined wavelengths with which aerosol particles, preferably bioaerosol such as bacteria, viruses, spores or pollen, are selectively excited.

Preferably, in the case of a thermal infrared emitter or an LED, for example, direct modulation can be performed by varying the current supply. This is also particularly easy and inexpensive to implement.

Modulation of the emitter can preferably also be achieved by external modulation, e.g. by using a rotating chopper wheel and/or an electro-optical modulator.

In a preferred embodiment, the modulable emitter allows wavelength-selective radiation and/or a wavelength-selective filter, such as a Fabry-Perot filter, is present in the beam path between the modulable emitter and the detection chamber.

The wavelength selective filter is preferably tunable. Thus, the photoacoustic gas sensor can be used to detect the presence and/or concentration of various aerosol particles, preferably bioaerosols, which can be excited at one or more wavelengths for the purpose of PAS. Advantageously, excitation by means of several wavelengths can also take place successively over time, such that the excitation can be tuned to the wavelength-dependent absorption behavior of the aerosol particles to be detected.

For example, a wavelength-sensitive infrared emitter may be a tunable laser and/or include multiple lasers of different wavelengths.

When using a tunable filter, an emitter with a broad spectrum can be used in particular, e.g. an LED and/or a thermal emitter in the case of an IR emitter.

In a preferred embodiment, the modulable emitter is a MEMS emitter.

MEMS technology refers in particular to a technology for the manufacture of compact, mechanical-electronic devices using microsystems technology. The microsystems (microelectromechanical systems, MEMS for short) that can be manufactured in this way are very compact (micrometer range) while at the same time offering outstanding functionality and ever lower manufacturing costs.

Both the emitter itself and micromechanical structures for its modulation can be provided by MEMS technology.

For example, the modulation of the intensity of the emitter can be performed by means of MEMS actuators that control a relative movement between an aperture structure and a radiation source (see, among others, EP 3623779 A1 or EP 36323780 A1).

By using MEMS actuators, for example an electrostatic actuator, a piezoelectric actuator, an electromagnetic actuator and/or a thermal actuator, a modulation of the intensity of the emitted infrared radiation can be achieved in a particularly fast and simple way. In particular, modulation frequencies of well over 100 Hz up to 100 kHz can be achieved. Such modulation frequencies are particularly advantageous in photoacoustic spectroscopy for increasing the signal-to-noise ratio. Thus, the modulation frequency of the emitter can be adjusted to a range that is further away from the inherent noise of the detection components of a sound detector, such as a microphone. In the case of microphones, the inherent noise is particularly high in the range from a few Hz to about 100 Hz.

In a preferred embodiment, the analysis volume represents an open system having one or more openings such that ambient air comprising aerosol particles can flow or diffuse into the analysis volume.

In a preferred embodiment, the analysis volume is an outwardly closed or closable volume (or chamber), at least in some areas, in which the ambient air is located or can be introduced, e.g. through one or more openings in the form, which can also be designed to be closable by a closure, valve and/or by a supply line.

The analysis volume is thus preferably at least partially open. In this way, a gas atmosphere (air) surrounding the spectroscope, the gas atmosphere having at least partial access to the analysis volume, can be measured and the amount or concentration of aerosol particles in it can be verified.

Advantageously, in this case, the analysis volume is well defined, such that the modulable emitter, the analysis volume and the sound detector are arranged in such a way that the radiation modulably emitted by the emitter can excite aerosol particles in the analysis volume to form sound pressure waves, which can be measured by means of the sound pressure detector.

The analysis volume is preferably located in the beam path of the emitter. This preferably means that the intensity of the beam is substantially or at least partially incident on the side of the analysis volume facing the emitter. Partially preferably means at least 40%, preferably at least 50%, 60%, 70%, 80% or more.

In a preferred embodiment, the emitter can be directed from the outside to a preferred region of the analysis volume. If it is necessary to radiate through an outer wall of the volume in order to excite the aerosol particles inside, the outer wall is preferably substantially transparent to the radiation (e.g. IR, UV and/or VIS) at least in this region. However, the emitter may also be present in the interior of the analysis volume.

In the case of an analysis volume which is at least partially open and thus preferably permits permanent gas exchange with its surroundings, filling of the analysis volume takes place by interaction with the gas atmosphere of its surroundings.

An analysis volume may preferably comprise a sample chamber and a reference chamber, which are connected or connectable by a connecting channel.

In the case of an embodiment of an analysis volume comprising a sample chamber and a reference chamber, it may be preferred to introduce at least one sound detector into each chamber in order to measure separately in each chamber and thus to be able to factor out sources of interference, e.g. external sound pressure waves which do not originate from the radiation absorbed in the sample chamber, preferably after the measurement.

It may also be preferred that the emitter irradiates the sample chamber and not the reference chamber, and wherein there is a connecting channel between the sample chamber and the reference chamber in which a sound detector is located. This embodiment is characterized by particularly precise photoacoustic spectroscopy, since, for example, sound from unwanted sound sources is factored out or not included in the measurement, during the measurement and/or the evaluation of the measurement. Preferably, sample volume and a reference volume can have substantially the same dimensions in order to realize an accurate differential measurement method.

The sample volume and the reference volume may contain the same gas. It may also be preferred that different gas is included in the sample volume and the reference volume, whereby a gas with known properties is present in the reference volume and a gas to be analyzed, preferably ambient air, is present in the sample volume. By using two volumes and at least one sound pressure detector, an improved elimination of error sources, e.g. undesired sound waves, can advantageously be achieved, because these act on both volumes and the sound pressure detector arranged between the volumes preferably detects substantially only the sound pressure waves in the sample volume caused by the selective excitation of the aerosol particles, which are relevant for photoacoustic spectroscopy, as a differential signal between sample volume and reference volume.

In a preferred embodiment, the photoacoustic gas sensor is characterized in that not only the sensor is implemented in MEMS technology, but the entire cell, in particular comprising an analysis volume, sample and/or reference chamber can be provided in a highly miniaturized form. Preferably, the largest dimension of the gas sensor is less than 5 cm, preferably less than 10 mm, less than 5 mm or less.

In particular, it is preferred that the entire photoacoustic gas sensor for detecting the aerosols is implemented as a MEMS. Advantageously, both the sensor can be realized or integrated directly in the MEMS. Furthermore, chambers for forming an analysis volume, a sample chamber and/or a reference chamber can preferably be formed in a multilayer substrate, the substrate designating in particular a base material for manufacturing the respective components. The term is oriented in particular to the semiconductor industry, in which circuits are manufactured from the substrate. In this context, materials and/or manufacturing techniques known from the semiconductor industry and/or MEMS manufacturing are used, which are suitable due to their efficiency, simplicity, low production costs and suitability for the production of large quantities.

In this context, a substrate can be processed and adapted in shape as desired by etching processes and/or physical processing techniques in one piece, in particular by removing and/or eliminating areas and/or layer thicknesses of the individual substrate. A multilayer substrate comprises in particular, multiple, preferably, 2, 3, 4, 5, 6, 7, 8, 9 or 10 layers or more of individual thin substrates, which can be individually machined and then assembled to form the gas sensor, in particular comprising said components.

In this way, for example, sample or reference chambers can be formed which have a height of 10 µm to 2 mm, preferably of 50 µm to 1 mm, particularly preferably of 100 µm to 500 µm and/or a length or width of 100 µm to 10 mm, preferably of 200 µm to 5 mm, particularly preferably of 500 µm to 2 mm. This allows at the same time a compact design and the formation of a sufficient volume for photoacoustic detection.

Preferably, a multilayer substrate can be formed by bonding at least two wafers. By bonding multiple layers of individually pre-processed substrates, advantageously complex components of gas sensors and in particular fully integrated, complete gas sensors can be easily manufactured.

The bonding of structures from pre-processed substrates allows the simple production of complex structures, which could be produced from a single wafer and/or substrate only with great complexity. In this way, cavities or chambers in the gas sensor can be provided by means of bonding without having to be elaborately machined out of the interior of a raw material.

It is possible to produce an easy to manufacture gas sensor with low height and high compatibility with other semiconductor elements such as electronic circuits. In preferred embodiments, a monolithic chamber with an integrated MEMS sensor can also be realized by suitably joining the substrate layers. Monolithic preferably means consisting of one piece, contiguous and/or seamless or inseparably assembled from very small components.

In a preferred embodiment, the MEMS sensor is a sound pressure detector, wherein the sound pressure detector preferably comprises a capacitively or optically readable piezoelectric, piezoresistive and/or magnetic beam and/or a capacitive, piezoelectric, piezoresistive and/or optical microphone.

The sound pressure waves generated by the PAS can preferably be detected in various ways. A sound pressure detector is a particularly suitable means. The sound pressure detector can in particular be a piezoelectric beam.

A piezoelectric beam is preferably a vibrating structure, in particular in the form of a bending beam, which comprises a piezoelectric material, e.g. in the form of an actuator.

It may be preferred that the bending beam is passive, which preferably means that it is caused to oscillate by the sound pressure waves. These in turn generate a voltage through the deformation of the piezoelectric material, which is based on the piezoelectric effect. The (direct) piezoelectric effect preferably describes the occurrence of an electrical voltage and/or a change in impedance on a solid made of corresponding material, when it is elastically deformed. The voltage can be tapped, for example, by suitable contacting and read out by a corresponding electronic circuit.

It may also be preferred that the bending beam is active, which means in particular that it is caused to oscillate due to the inverse piezoelectric effect. The piezoelectric effect preferably describes the deformation of a material when an electrical voltage and/or an electrical field is applied, as a result of which a force can be exerted in particular by the material. The sound pressure waves can preferably cause a variation in the damping of the vibrating beam, which can be measured, e.g. by a change in the resonant frequency of the vibrating beam.

A beam that vibrates passively due to sound pressure waves can preferably also be read out, e.g. by capacitive, magnetic and/or piezoresistive methods. Here, the vibrations can produce an electrically readable change, e.g. based on a changing magnetic flux through a resonating magnet, by a changing capacitance between a vibrating and a fixed electrode and/or by a changing electrical resistance in a piezoresistive material.

A microphone preferably comprises a vibrationally mounted membrane, which is excited to vibrate by sound pressure waves, which in turn can be read out electrically, similar to the beam described above. Capacitive, piezoelectric and/or piezoresistive measurement methods of the mount design can also be used.

Preferably, an optical microphone can also be used, whereby these vibrations can preferably be converted into an optical signal by reflection, e.g. of a laser beam on the membrane, which is read out, e.g. in an interferometric arrangement.

In another preferred embodiment of the invention, the MEMS sensor is a capacitive microphone comprising a MEMS membrane as electrode as well as a counter electrode and wherein the MEMS membrane preferably has a maximum dimension in at least one direction of 100 μm to 1500 μm, in particular 200 to 1000 μm.

Due to the preferred absence of mechanical components, MEMS sensors of these embodiments are particularly easy and compact to manufacture while being very robust.

In another aspect, the invention relates to a photoacoustic gas sensor for detecting aerosol particles in ambient air by means of the method described comprising
  a modulable emitter,
  an analysis volume which is in fluid communication with the ambient air
  a MEMS sensor for the detection of sound pressure waves,
  wherein the detection chamber is present in the beam path of the emitter so that the emitter can use modulable radiation to excite aerosol particles in the analysis volume to form sound pressure waves which are detectable by means of the sensor.

The average person skilled in the art will recognize that technical features, definitions, and advantages of preferred embodiments of the method of the invention for detecting aerosols in ambient air also apply to the photoacoustic gas sensor, and vice versa.

In a preferred embodiment, the photoacoustic gas sensor comprises a control unit configured to control the emitter to selectively excite and detect the aerosol particles, wherein the wavelength of the emitted radiation is tuned to the absorption behavior of the aerosol particles to be detected.

The control unit is preferably a unit which is suitable and configured for receiving, processing, generating and/or transmitting control signals, preferably measurement data. The control unit preferably comprises a processor, for example a microprocessor, for this purpose. Other integrated circuits, which are used in digital electronics for control, can also be used. A control unit, in particular in the form of a controller integrated in the emitter, is very compact and easy to handle.

For input, the control unit preferably has a suitable interface for connection to a computer, for example. It may also be desired that data can be transmitted also from the control unit to an input device via this interface, such as the modulation frequency, one or more wavelengths for selective excitation or other status information.

The use of a suitable control unit can greatly simplify the desired use of the spectrometer. For example, suitable spectroscopy signals can be designed on a PC. The desired signals are transmitted to the control unit via an input module. The control unit generates drive signals which ensure selective excitation of aerosol particles, whereby the wavelength of the emitted radiation is tuned to the absorption behavior of the aerosol particles to be detected.

Preferably, the control of a wavelength-selective emitter and/or filter can be based on reference data reflecting the spectral fingerprint of the aerosol particles to be detected. The control signals can preferably be set in such a way that the excitation takes place at one or more wavelengths at which a pronounced PAS signal is to be expected for the aerosol particle to be detected.

In a preferred embodiment, the photoacoustic gas sensor comprises a data processing unit configured to make a determination about the presence and/or concentration of aerosol particles in the ambient air based on an evaluation of measurement results for the generated sound pressure waves.

The data processing unit is preferably a unit which is suitable and configured for receiving, transmitting, storing and/or processing data, preferably measurement data. The data processing unit preferably comprises an integrated circuit, a processor, a processor chip, microprocessor or microcontroller for processing data, and a data memory, for example a hard disk, a random access memory (RAM), a read-only memory (ROM) or also a flash memory for storing the data.

In order to perform the evaluation of the measurement results of the generated sound pressure waves and to determine the presence and/or concentration of aerosol particles in the ambient air, a computer program can preferably be stored on the data processing device, which includes commands to execute the above steps.

The data processing unit and control unit can preferably use the same processor.

In particular, reference data are preferably available on the data processing unit. Reference data preferably refers to all data which allow the presence and/or concentration of aerosol particles in the ambient air to be determined.

As explained above, such reference data can preferably be obtained from calibration measurements in which the photoacoustic gas sensor is placed in a controlled volume with a known concentration of the aerosol particle to be detected. By performing a PAS at one or more wavelengths under such controlled conditions, reference values can be obtained for a characteristic PAS spectrum of aerosol particles to be detected, preferably correlating the amplitude of the PAS signals at the selective wavelengths with the concentration of the aerosol particles.

By comparing the measurement data with the reference data or reference values, it can be advantageously determined whether the aerosol particles to be detected are in the ambient air and, if so, in what concentration.

In the context of the invention, the determination of a presence preferably means a statement as to whether the measurement data indicate an increased probability for the presence of aerosol particles in the analysis volume. Preferably, this is given by measurement of an increased PAS signal at one or more of the selective wavelengths compared to reference data under conditions in which no or at least no measurable aerosol particles are present in the ambient air. A concentration of aerosol particles preferably means a quantitative statement about the amount (e.g., number or mass) of aerosol particles for a volume of ambient air. This can, but does not have to include a statement about absolute values of the concentration, but can also refer to a relative concentration compared to reference concentrations.

In preferred embodiments, the photoacoustic gas sensor may comprise a signal generator, wherein the data processing device is configured to generate a warning signal by means of the signal generator if the determined concentration of aerosol particles in the ambient air exceeds a predetermined threshold.

The signal generator for outputting a warning signal may include a speaker or a visual display to generate an immediate warning at the photoacoustic gas sensor. However, the signal generator can also forward the warning signal as a digital or analog electrical signal to a central data processing unit so that further suitable protective measures can be triggered on the basis of the warning signal.

DETAILED DESCRIPTION

In the following, the invention will be explained in more detail by means of examples and figures, without being limited to them.

Figure 1:
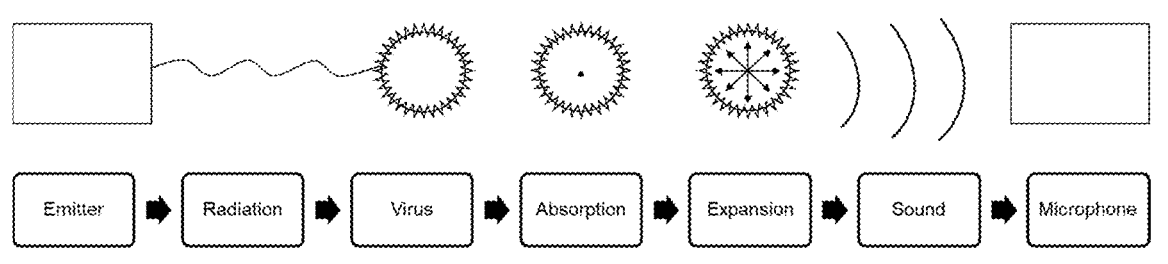

FIG. 1 is a schematic illustration of a preferred embodiment of the method for the detection of aerosol particles in ambient air, using the example of a virus.

Electromagnetic radiation is generated by means of a modulable emitter, in particular in the infrared, visible or ultraviolet wavelength range. The emitter is preferably arranged and configured so that the radiation emitted by the emitter is substantially incident on the analysis volume. If the modulated irradiation occurs at a wavelength corresponding to the absorption spectrum of a virus located in the analysis volume, modulated absorption takes place, resulting in heating and cooling processes whose time scales reflect the modulation frequency of the radiation. In particular, the protein envelope of viruses can absorb the electromagnetic radiation and lead to expansion.

According to the photoacoustic effect, the heating and cooling processes lead to expansions and contractions of components of the virus (in particular the proteins of the protein envelope) or of the entire virus, resulting in the formation of sound pressure waves with essentially the modulation frequency. The sound pressure waves can be measured by a sound detector, e.g. a microphone. The power of the sound waves is preferably directly proportional to the concentration of the viruses in the analysis volume.

FIG. 2 illustrates the different sizes and types of aerosol particles that can advantageously be detected with the method according to the invention.

LITERATURE

Tobias, H. Bioaerosol mass spectrometry for rapid detection of individual airborne *Mycobacterium tuberculosis* H37Ra particles. *Appl. Environ. Microbiol.* 71, 6086-6095 (2005).
Fernstrom A. et al, Aerobiology and Its Role in the Transmission of Infectious Diseases Journal of Pathogens Volume 2013, Article ID 493960, 13 pages.
Senguptaa, A., Brarb, N. & Davis, E. J. Bioaerosol detection and characterization by surface-enhanced Raman spectroscopy. *J. Colloid Interface Sci.* 309, 36-43 (2007).
Schafer, M. P. et al. 1999. detection and characterization of airborne *Mycobacterium tuberculosis* H37Ra particles, a surrogate for airborne pathogenic *M. tuberculosis*. Aerosol Sci. Technol. 30:161-173.
Park, Kyu-Tae et al. Detection of airborne viruses using electro-aerodynamic deposition and a field-effect transistor, Scientific Reports|5:17462|DOI: 10.1038/srep17462.
Huffman et al Real-time sensing of bioaerosols: Review and current perspectives AEROSOL SCIENCE AND TECHNOLOGY 2020, VOL. 54, NO. 5, 465-495.
MARSH, D. G. (1975). Allergens and the genetics of allergy; in M. Sela (ed), The Antigens, Vol. 3, pp 271-359. (Academic Press Inc., London, New York).

The invention claimed is:

1. A method for a detection of aerosol particles in ambient air, comprising
   a. providing a photoacoustic gas sensor comprising,
      a modulable emitter,
      an analysis volume which is in fluid communication with the ambient air, wherein the analysis volume is an open system having one or more opening(s) such that the ambient air comprising aerosol particles can flow or diffuse into the analysis volume,
      a MEMS sensor for the detection of sound pressure waves,
      wherein the analysis volume is present in a beam path of the emitter such that the emitter can use modulable radiation to excite aerosol particles in the analysis volume to form sound pressure waves which are detected by the MEMS sensor,
   b. irradiating the analysis volume with radiation modulated with a modulation frequency to generate sound pressure waves
   c. measuring the generated sound pressure waves by the MEMS sensor
   d. determining a presence and/or concentration of aerosol particles in the ambient air based on measurement results,
   wherein the aerosol particles are bioaerosols and wherein a selective excitation and a detection of the aerosol particles is performed by tuning a wavelength of an emitted radiation to an absorption behavior of the aerosol particles.

2. The method according to claim 1, wherein the aerosol particles are pollen, spores, bacteria or viruses.

3. The method according to claim 1, wherein the aerosol particles are bioaerosols, preferably pollen, spores, bacteria or viruses, wherein the wavelength of the emitted radiation for the selective excitation is selected from a range between 170 nm and 1000 nm.

4. The method according to claim 1, wherein the modulable emitter permits wavelength-selective radiation and/or wherein a wavelength-selective filter is present in a beam path between the emitter and the analysis volume.

5. The method according to claim 4, wherein the wavelength-selective filter is a Fabry-Perot filter.

6. The method according to claim 1, wherein the modulable emitter is an infrared emitter or a UV emitter.

7. The method according to claim 1, wherein the MEMS sensor is a sound pressure detector.

8. The method according to claim 7, wherein the sound pressure detector comprises a capacitively or optically readable piezoelectric, piezoresistive and/or magnetic beam and/or a capacitive, piezoelectric, piezoresistive and/or optical microphone.

9. A photoacoustic gas sensor for detecting aerosol particles in ambient air by a method according to claim 1, comprising
   a modulable emitter,
   an analysis volume which is in fluid communication with the ambient air, wherein the analysis volume is an open system having one or more openings such that ambient air comprising aerosol particles can flow or diffuse into the analysis volume,
   a MEMS sensor for the detection of sound pressure waves, wherein the detection chamber is present in a beam path of the emitter such that the emitter can use modulable radiation to excite aerosol particles in the analysis volume to form sound pressure waves which can be detected by the MEMS sensor, wherein the aerosol particles are bioaerosols and wherein the photoacoustic gas sensor comprises a control unit configured to control the emitter to selectively excite and detect the aerosol particles, wherein the wavelength of the emitted radiation is tuned to the absorption behavior of the aerosol particles to be detected.

10. The photoacoustic gas sensor according to claim 9, wherein the photoacoustic gas sensor comprises a data processor configured to make a determination about the presence and/or concentration of the aerosol particles in the ambient air based on an evaluation of measurement results for the generated sound pressure waves.

11. The photoacoustic gas sensor according to claim 9, wherein the photoacoustic gas sensor comprises a signal generator, the data processor being configured to generate a warning signal by the signal generator if the detected concentration of the aerosol particles in the ambient air exceeds a predetermined threshold.

\* \* \* \* \*